United States Patent [19]

Piatt

[11] Patent Number: 4,934,564

[45] Date of Patent: Jun. 19, 1990

[54] DROP JET METERING METHOD AND SYSTEM

[75] Inventor: Michael J. Piatt, Enon, Ohio

[73] Assignee: Eastman Kodak Company, Rochester, N.Y.

[21] Appl. No.: 327,868

[22] Filed: Mar. 23, 1989

[51] Int. Cl.$^5$ .................. B67D 5/30; B67D 47/18
[52] U.S. Cl. ........................ 222/14; 222/37; 222/420
[58] Field of Search ............... 222/14, 36, 37, 420; 417/52

[56] References Cited

U.S. PATENT DOCUMENTS

| | | | |
|---|---|---|---|
| 3,476,291 | 11/1969 | Glaser | 222/14 |
| 3,736,930 | 6/1973 | Georgi | 222/14 |
| 4,331,262 | 5/1982 | Snyder et al. | 222/37 |
| 4,432,699 | 2/1984 | Beckman et al. | 417/63 |
| 4,432,761 | 2/1984 | Dawe | 222/420 |
| 4,433,795 | 2/1984 | Malefski et al. | 222/14 |
| 4,446,993 | 5/1984 | Tokorozawa | 222/420 |
| 4,449,893 | 5/1984 | Beckman et al. | 417/322 |
| 4,475,666 | 10/1984 | Bilbrey et al. | 222/14 |
| 4,498,843 | 2/1985 | Schneider et al. | 222/14 |
| 4,723,129 | 2/1988 | Endo et al. | 417/52 |

*Primary Examiner*—Michael S. Huppert
*Assistant Examiner*—Steven Reiss
*Attorney, Agent, or Firm*—John D. Husser

[57] ABSTRACT

A dispensing system for metering precise quantitites of liquid to a use site in droplet streams. The system includes a reservoir containing a quantity of liquid to be dispensed, a droplet generator for producing a stream of uniformly sized droplets of the liquid in the reservoir; and a device for controlling the droplet generator to produce a droplet stream containing a predetermined number of droplets. The control device can include an operator-settable counter for selectively varying the quantity of dispensed liquid by adjusting the number of produced droplets or by adjusting the size of droplets comprising the droplet stream.

4 Claims, 3 Drawing Sheets

FIG. 5
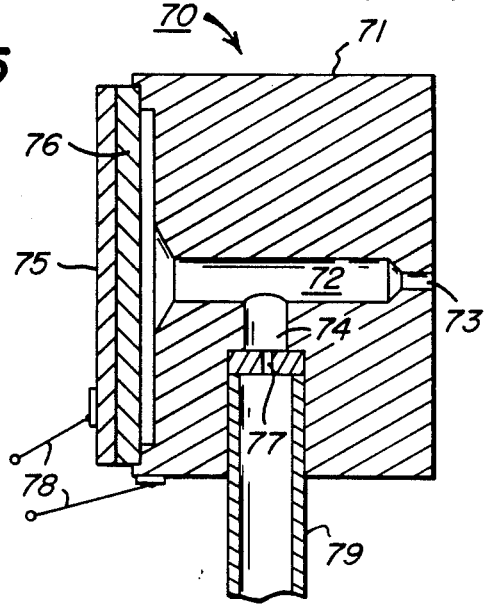
FIG. 7
DROP VOLUME DISTRIBUTION
$\overline{V}_3$
FIG. 6
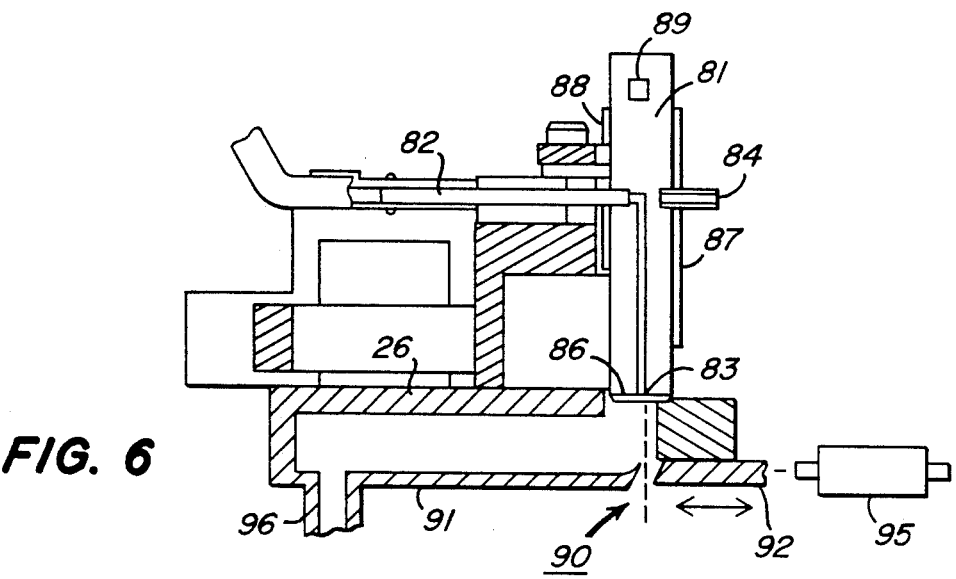

DROP JET METERING METHOD AND SYSTEM

FIELD OF THE INVENTION

The present invention relates to methods and systems for metering relatively small and precise quantities of liquid, for example, for uses in the scientific, industrial or medical fields; and, more particularly, to drop jet approaches for selectively supplying predetermined numbers of uniform volume droplets to accurately accumulate the desired quantity of liquid.

BACKGROUND OF INVENTION

There are a broad spectrum of technical and medical endeavors that require application of exact quantities of liquids For example, the dyeing of slides for microscope work, the applying of catalyst to cure epoxies and the administering of drugs, all require that precise amounts of a critical liquid(s) be metered to a predetermined use site. Present technology devices for accomplishing these tasks include syringes, brushes, pipets and "eye droppers". To provide accuracy of application within a requisite quantity range, it is often necessary to substantially dilute the use liquid in a carrier and supply more volume of the carrier/use liquid combination.

A more sophisticated approach for controlled dispensing of liquids is described in U.S. Pat. No. 4,475,666, which uses a microcomputer controlled motor to operate the piston of a syringe. This system has a detection and feedback loop that monitors and controls the piston drive motor to assure accurate ejection of the quantities selected (i.e. entered into the system microcomputer) by the user. This system is relatively complicated structurally and requires servo systems that compensate for mechanical backlash and motor drive variations.

SUMMARY OF THE INVENTION

It is an object of the present invention to provide simple, but accurate, liquid metering methods and systems that utilize liquid droplet streams of the kind heretofore used in ink jet printing technologies. Thus, I have realized that by accurately controlling the number of minute liquid droplets ejected by such jetting system to a use site, very precise overall quantities of liquid can be conveniently and accurately metered.

In one aspect the present invention constitutes a method of dispensing precisely metered quantities of a liquid to a use site by: (a) generating a stream of uniformly sized droplets of the liquid; and (b) controlling such droplet stream so that a predetermined number of droplets pass to the use site.

In another aspect the present invention comprises a dispensing system for metering precise quantities of liquid to a use site. The system comprises a reservoir for containing a quantity of liquid to be dispensed; a droplet generator for producing a stream of uniformly sized droplets from liquid in the reservoir; and a circuit for controlling the generator to dispense a droplet stream containing a predetermined number of droplets.

BRIEF DESCRIPTION OF DRAWINGS

The subsequent description of preferred embodiments refers to the accompanying drawings wherein:

FIG. 5 is an enlarged cross sectional view of another preferred applicator device for practicing the invention;

FIG. 6 is a cross sectional view of another applicator embodiment for practicing the present invention; and FIG. 7 is a diagram useful for explaining the applicator system of the present invention.

DETAILED DESCRIPTION OF PREFERRED EMBODIMENTS

Figure 1:
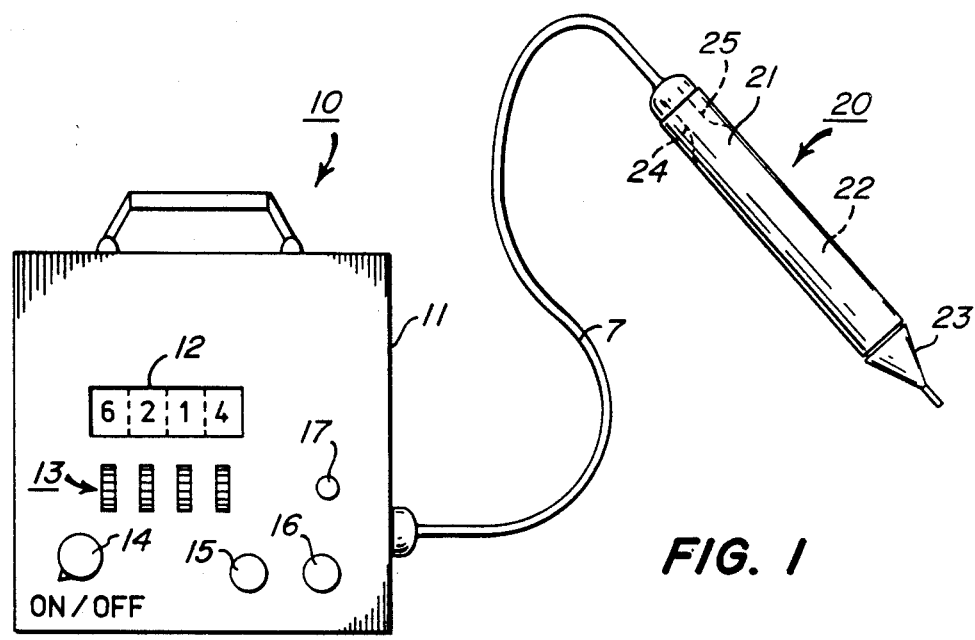
FIG. 1 is a schematic illustration of one preferred metering system for implementing the present invention.

Referring to FIG. 1, a portable metering system constructed in accord with the present invention is shown schematically. The system, in general, includes a power and control assembly 10 and a droplet dispenser device 20, connected by an electrical umbilical 7. The assembly 10 is contained in a housing 11 and has a drop count display 12, dials 13 for setting the desired number of drops to be dispensed, an on-off switch 14, drop amplitude, frequency adjustment knobs 15, 16 and start button 17. The dispenser device 20 comprises, in general, a hand-held housing 21, a liquid reservoir 22, a drop dispensing head 23 and electrodes 24, 25 for coupling the head 23 to the umbilical 7.

Figure 2:
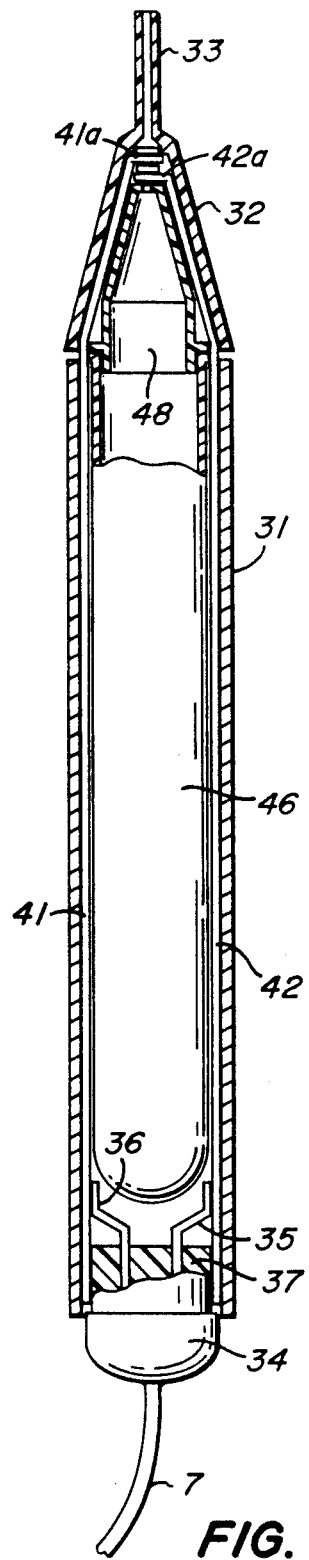
FIG. 2 is an enlarged cross sectional view of the applicator device of the FIG. 1 system.
Figure 3:
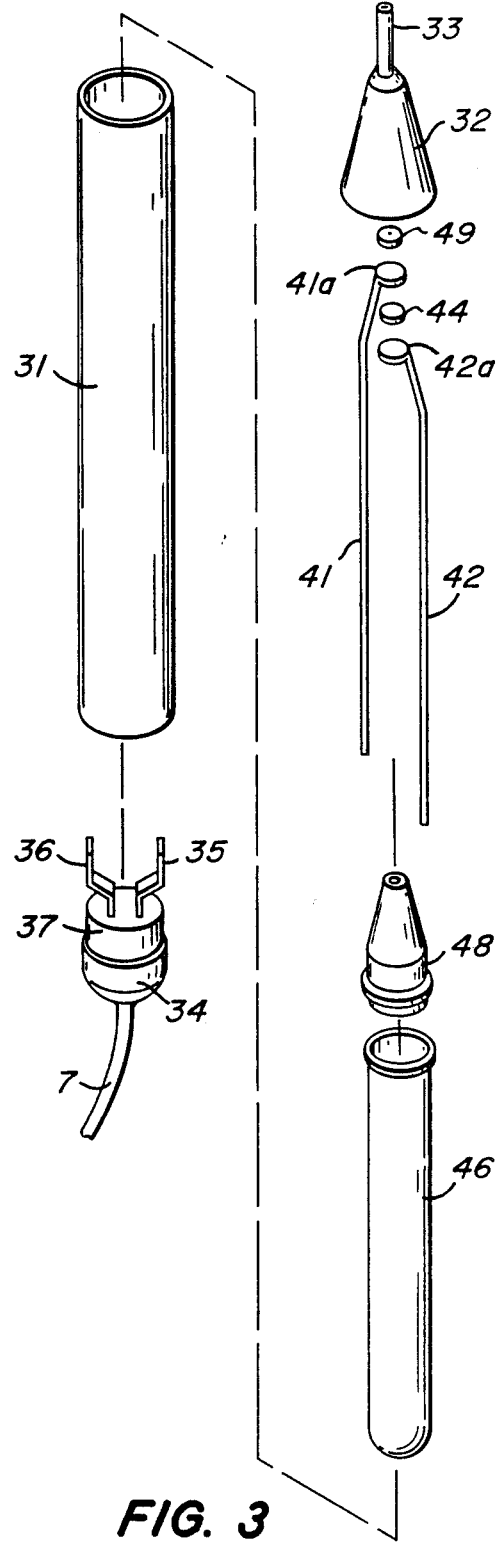
FIG. 3 is an exploded perspective view of the FIG. 2 applicator.

One preferred construction for a thermal drop-on-demand dispensing device 20 is shown in detail in FIGS. 2 and 3. There it can be seen that the device housing comprises an elongated cylindrical shell 31, a top cap 32 having a hollow tip 33 and an end cap 34 having terminals 35, 36 coupled to the umbilical 7 and a stopper plug 37. Constructed to interfit within the housing portions, as shown in FIGS. 2 and 3, are a plurality of device elements for selectively thermally ejecting drops of a liquid. Thus electrodes 41, 42 are constructed to couple to terminals 36, 37 and have top portions 41a, 42a constructed to sandwich, and selectively energize, a resistive heater element 44. A flexible liquid reservoir 46 with an open top is constructed to fit within shell 31 and between electrodes 41, 42. A hollow spacer 48 is constructed to retain the top of reservoir bladder 46 and to support an orifice plate 49 above the heater and electrode sandwich. The electrode tops 42a and 41a have, respectively, groove and slot openings which allow liquid to flow along a tortuous path from the bladder 46 to a location between the heater 44 and orifice 49. Upon energization of the heater element, a liquid bubble ejects a drop of the liquid in a known manner and the tortuous liquid supply path restricts back flow.

Figure 4:
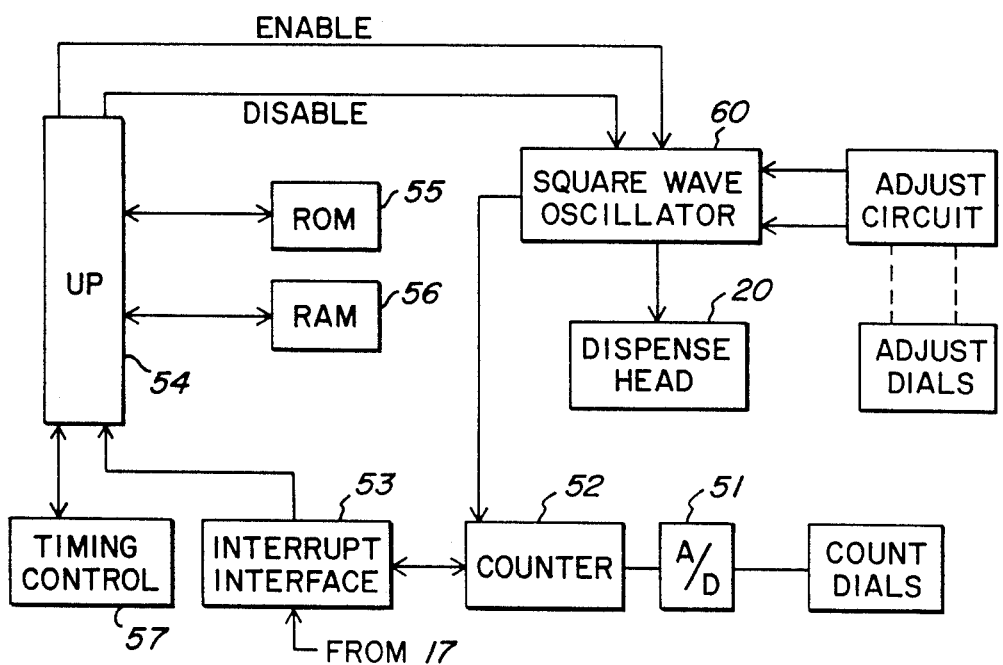
FIG. 4 is a schematic diagram of the control circuits for the FIG. 1 system.

The operation of the dispenser device to effect metering of desired quantities of liquid to a use site can be further understood by referring to the control system circuit shown in FIG. 4. Thus, to commence a dispensing operation, top cap 33 and spacer 48 are removed and a supply of the liquid to be dispensed is filled into bladder 46. When the cap and spacer are replaced, the power switch 14 is actuated and counter dials 13 are set to a predetermined value representing the number of drops to be dispensed. The dial settings are converted to a digital signal by A/D device 51 and set the counter 52 to a pulse count total equal to the selected drop dispense number of the dials.

Next, the tip of device 20 is placed on the use site and the start button 17 is actuated to send a start signal, then via interrupt interface 53, to microprocessor 54. In accord with a drop dispense program stored in ROM 55 and under the regulation of timing control 57, the microprocessor enables square wave oscillator 60 to produce a train of square pulses The oscillator 60 includes power amplifier states and outputs a drive pulse train to the dispense head, as well as a countdown pulse train to counter 60.

The drive pulse train provides a continuing series of energizations of heater 44, each with a corresponding liquid drop ejection to the use site. The drop ejections continue until counter 52 has been returned to a zero count by the countdown pulse train from oscillator 60. When the zero count occurs, counter 52 signals microprocessor 54 to disable oscillator 60, which stops the drop dispense sequence. If desired, a predetermined number of dispensing sequences of the same drop count can be selected by inputting the number of sequences into RAM 56. In this event, the original drop count selection is stored in RAM 56 along with the number of dispense repetitions and the counter is reset by the microprocessor automatically, e.g. after a predetermined time delay to provide a new use site for the dispense device 20.

The physical mechanism of drop ejection used by the FIG. 2 dispense device 20 is often referred to in the art as "bubble jetting". U.S. Pats. No. 4,243,994 and 4,740,796 provide a further disclosure of this mechanism and of other structural configurations for effecting it. For practice of the present invention, the bubble jet approach is desirable for dispensing liquids that have the appropriate boiling point and decomposition point characteristics described in the '994 patent. An exemplary liquid that can be dispensed by the bubble mechanism is:

A Liquid Useful for Bubble Jet

X%: Material to be dispensed
50%: Diethylene Glycol
0.1-1%: Sodium Omadine (Sodium-2-Pyridinethiol-1-oxide) (for bacteria control)
0.1-0.2%: Cobratec TT-50S (Tolyltriazole) (to control corrosion)
0.1-2.0%: Triethanolamine (to control pH)
Balance: Pure Solvent FIG. 5 shows an alternative drop dispensing head which can be used in practice of the present invention. In this embodiment drop ejection is effected by deflection of a piezoelectric element. Thus, the drop ejecting device 70 comprises a housing 71 forming a drop ejection chamber 72, a drop ejection nozzle 73 and a supply passage 74. A metal plate 75 at the rear of the drop ejection chamber has piezoelectric crystal 76 which is coupled by electrodes 78 to receive a sequence of voltage pulses in the same manners as described with respect to the current pulse applied to the heater of the FIG. 2 embodiment. In response to a voltage pulse, the crystal 76 deflects metal plate toward the orifices 73 causing a discrete drop ejection. Liquid to be dispensed is supplied to the inlet passage 74 of the device 70 by a supply tube 79, e.g. by gravity or under fluid pressure. An inlet orifice 77 provides resistance to back flow during drop ejection. Further description of drop ejection devices such as shown in FIG. 5 is provided in U.S. Pat. No. 3,747,120. A number of other different piezoelectric drop on demand devices are useful for practice of the invention and are fairly versatile in regard to the characteristics of liquids handled. An exemplary liquid useful with piezoelectric DOD heads is:

Liquid Useful for Piezoelectric DOD Heads

X%: Material to be dispensed
1-4%: Diethylene Glycol
0.1-1.0%: Sodium Omadine (Sodium-2-Pyridinethiol-1-oxide)
0.1-2.0%: Cobratec TT-50S
0.1-2.0%: Triethanolamine
Balance: Pure Solvent In certain dispensing applications, dispensing drop ejection systems similar to continuous ink jet printers is useful. FIG. 6 illustrates one approach for employing such continuous jet approaches to accurate metering for liquid dispensing. Thus, continuous Jet device 80 includes a resonator block 81 having an inlet 82 for receiving liquid under pressure and directing it to an orifice manifold region 83 and thence to a liquid return outlet 84. The liquid supplied to the manifold region discharges toward a use site as a liquid filament(s) through an orifice(s) in an orifice plate 86.

The resonator block has a pair of piezoelectric strips 87, 88 which are energized by a voltage pulse train to vibrate the resonator and orifice plate at a predetermined frequency. The issuing liquid filament breaks into a stream of liquid drop of uniform size and a spacing which corresponds to the vibration frequency. A piezoelectric feedback tab 89 provides a signal to servo the drop rate and the vibration signal.

In accord with the present invention, a predetermined number of drops is dispensed by controlling the opening and closing of the drop stream passage 90 to the use site. Thus, a catch pan 91 and a slidable shutter member 92 are constructed between the orifice 86 and the use site. The shutter member is slidable between a position blocking the drop stream and the illustrated position opening the drop stream passage to the use site. The shutter is actuated between positions by a fast acting solenoid 95 and, when closed, directs liquid drops to drain outlet 96 to be returned to the liquid supply for recirculation.

The control system for the device of FIG. 6 operates in a manner similar to the system shown in FIG. 4. In this embodiment the oscillator signal is applied to the resonator and to the counter. After the Jet stream is stabilized the shutter is opened and the counter begins to count down in accord with the resonator pulse train When a predetermined drop count is reached (i.e. a known interval before the desired drop count), the microprocessor actuates solenoid 90 to commence closure. The shutter 92 is then moved to block the drop stream at the proper time to achieve the desired drop quantity to reach the use site. An exemplary liquid useful in a continuous jet dispensing system is:

Liquid Useful for a Continuous Jet Dispensing System

X%: Material to be dispensed
1-4%: Polyethylene Glycol (Viscosity Modifier)
0.1-1%: Sodium Omadine (Sodium-2-Pyridinethiol-1-oxide) (for bacterial control)
0.1-0.2%: Cobratec TT-50S (Tolyltriazole) (for corrosion inhibition)
1.0-2.0%: ION Solution Sodium Hydroxide
Balance: High Purity Solvent The invention has been described in detail with particular reference to preferred embodiments thereof, but it will be understood that variations and modifications can be effected within the spirit and scope of the invention.

I claim:

1. A dispensing system for metering precise quantities of liquid to a use site, said system comprising:
   (a) a droplet dispenser device including:
      (i) hand-held housing means;
      (ii) a reservoir within said housing for containing a quantity of liquid to be dispensed; and
      (iii) droplet generator means for producing a stream of uniformly sized droplets of liquid in said housing means reservoir;
   (b) power and control means, external to said housing means, for controlling said droplet generator to produce a droplet stream containing a predetermined number of such droplets; and
   (c) umbilical means for connecting said droplet dispenser device and said power and control means.

2. The invention defined in claim 1 wherein said power and control means includes operator-settable counter means for selectively varying the quantity of dispensed liquid by adjusting the number of produced droplets.

3. The invention defined in claim 1 wherein said power and control means includes means for adjusting said drop generator means to selectively change the uniform size of droplets comprising said droplet stream.

4. The invention defined in claim 1 wherein said power and control means includes means for adjusting said drop generator means to selectively change the rate of drop generation thereof.

* * * * *